United States Patent [19]
Andreev et al.

[11] 3,941,089
[45] Mar. 2, 1976

[54] COLLECTOR FOR IMAGOS AND THE EGGS THEREOF

[76] Inventors: Sergei Vasilievich Andreev, Leningrad; Mikhail Grigorievich Leibenzon, Moskovskoi Oblasti; Jury Petrovich Trushin, Moscow; Mikhail Sergeevich Luzgin, Leningrad, all of U.S.S.R.

[22] Filed: Oct. 25, 1973

[21] Appl. No.: 409,450

Related U.S. Application Data

[63] Continuation of Ser. No. 323,402, Jan. 15, 1973, abandoned.

[52] U.S. Cl. ................................. 119/1; 119/15
[51] Int. Cl. ........................................ A01k 29/00
[58] Field of Search ........................... 119/1, 15

[56] References Cited
UNITED STATES PATENTS

| | | | |
|---|---|---|---|
| 1,974,549 | 9/1934 | Spencer et al. | 119/1 |
| 2,539,633 | 1/1951 | Morrill | 119/1 |
| 2,970,565 | 2/1971 | Reynolds | 119/1 |

*Primary Examiner*—Hugh R. Chamblee
*Attorney, Agent, or Firm*—Holman & Stern

[57] ABSTRACT

The proposed collector incorporates a chamber and an auxiliary compartment; located on the bottom of said chamber is a screen conveyer for images to lay eggs thereon, said conveyer being driven by drive shafts located in the auxiliary compartment; apart from said shafts the compartment accommodates also brushes adapted for removing eggs from the conveyer screens, containers for taken-off eggs, a bath with washing liquid for cleaning the screen conveyer, a heater fan for drying the conveyer upon its having been cleaned by washing, and tensioning means which are adapted for equalizing the tension of the conveyer screens.

2 Claims, 1 Drawing Figure

U.S. Patent  March 2, 1976  3,941,089
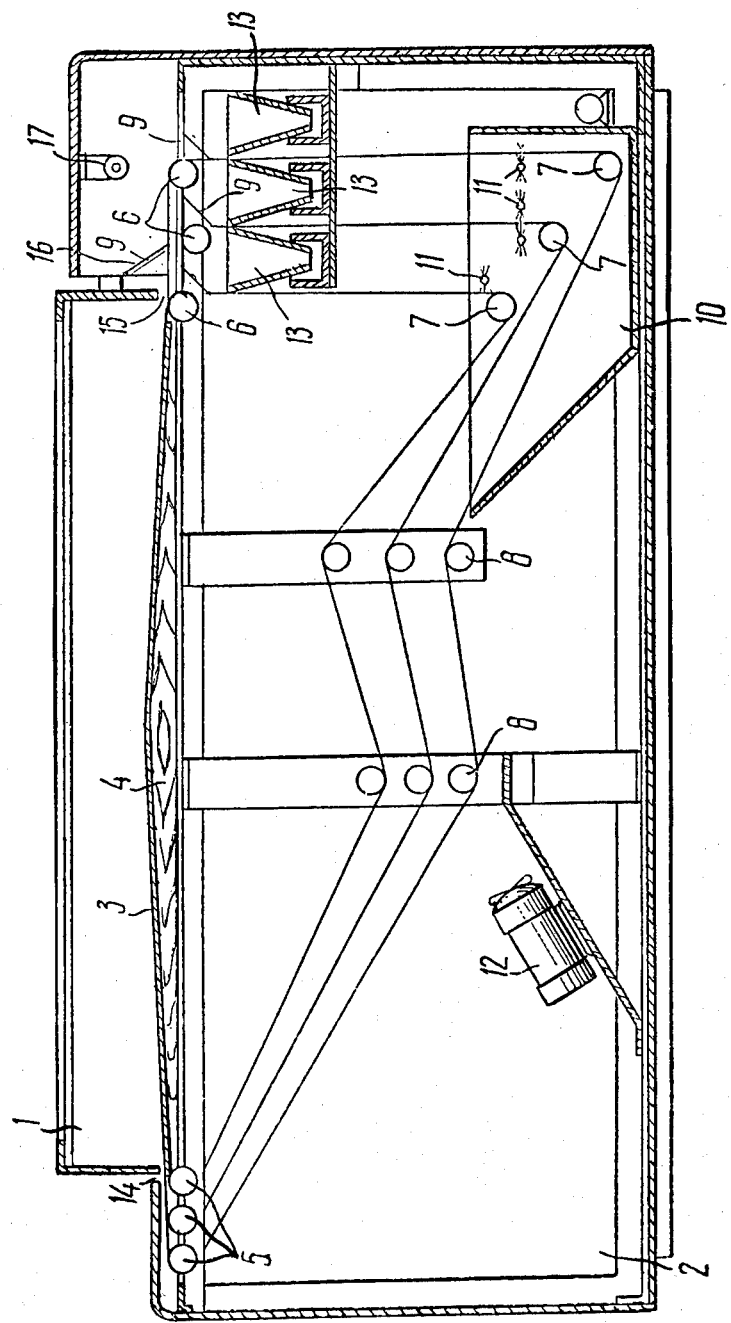

COLLECTOR FOR IMAGOS AND THE EGGS THEREOF

This is a continuation of application Ser. No. 323,402, filed Jan. 15, 1973, now abandoned.

The present invention relates generally to the sphere of farming practice and more specifically to devices for artificial propagation of insects.

For propagation of useful insects a host insect is needed, for which purpose, say, grain moth is reproduced under artificial conditions.

A collector for imagos and the eggs thereof, comprising a chamber with an inlet tube for the imagos to enter from an outer insect-conveying duct and an endless conveyor which incorporates a screen and a supporter for the imagos to lay eggs thereon. The conveyor is driven by drive shafts located in an auxiliary compartment which is located beneath the chamber and also accommodates rotary brushes to take off the eggs from said conveyor, and containers to hold the picked eggs and dead imagos therein is known in the art.

(Cf. USSR Inventor's certificate No. 254,939).

Due to said known device it has been made possible to reproduce insects under optimum conditions therefor and, besides, to make this labour-consuming process mechanized.

However, said device suffers from a substantial disadvantage residing in that the screen conveyer whereon the moth images are to lay eggs, is liable to get dirty with time, the screen meshes become clogged, all this impairing the yield of eggs and resulting in deteriorated quality thereof.

It is an essential object of the present invention to provide a device capable of ensuring proper conditions for an increased amount of eggs obtained and a higher quality thereof.

Said object is accomplished due to the fact that the rotary brushes for picking the eggs are provided both in between and behind the drive shafts of the screen conveyor which shafts are arranged parallel to each other at different levels with respect to the chamber bottom, while the auxiliary compartment is additionally provided with a washing liquid bath for cleaning the conveyor having brushes therein between which the screens cleaned of eggs and dead imagos and the supporter pass, said screens being isolated from each other on the drive shafts of said conveyer, and a heater fan to dry said screens and the supporter each of which envelopes tension shafts adapted to equalize the degree of tension of the screens and the supporter that have been cleaned by washing.

The herein-disclosed collector makes it possible to improve the quality of the eggs obtained and increase the amount thereof which is attainable due to a continuous cleaning of the screen conveyer by the proposed system of the brush cleaners.

It is advisable that the bottom of the chamber be made at a radius of curvature not above 10 m.

Due to the fact that the bottom of the chamber is made at a definite radius of curvature, the screens adhere evenly to the supporter over the entire chamber bottom area.

Other objects and advantages of the invention will now be disclosed in the following detatiled description of certain specific embodiments thereof having reference to the accompanying drawing, wherein a longitudinal-section view of a collector for imagos and the eggs thereof, according to the invention is represented.

The herein-proposed collector for imagos and the eggs thereof comprises an enclosure defining a chamber 1 and an auxiliary compartment 2 located thereunder.

The chamber 1 is made of organic glass. Located on a bottom 4 of the chamber 1 are two movable capron screens and a supporter 3, all of these being made as endless belts. The supporter is made of fiberglass fabric impregnated with polyethylene. The chamber bottom 4 is made of Duralumin and is convex at a radius of 10 m.

The supporter and the screens 3 envelope driven shafts 5 and drive shafts 6 at the butt ends thereof, both shafts imparting motion to the supporter and the screens.

The drive shafts 6 receive motion from electric motors located in the auxiliary compartment 2.

Said compartment 2 accommodates also guide shafts 7 and tension shafts 8 for said screens and said supporter 3, rotary brushes 9 adapted for taking off the laid eggs from the screens and the supporter 3, a bath 10 containing washing liquid and provided with stationary brushes 11, as well as a heater fan 12 to remove moisture from the screens and the supporter 3 that have been cleaned by washing.

We have established that said rotary brushes 9 adapted for taking off the eggs from the strainers 3 is more advantageous to be made as cylinders having two diametrally opposite rows of bristle. Besides, the arrangement of said brushes in the auxiliary compartment 2 is so selected that, when the brushes are rotating, their bristle touches the supporter on one side and the screens on both sides. With due account for said features the stationary brushes 11 are mounted in the bath 10 containing washing liquid.

Further on, located under the rotary brushes 9 for taking off the eggs are containers 13 for the eggs and dead imagos.

At one of its butt ends the chamber 1 has two openings; via one of these imagos are fed from the outer insect-conveying duct by way of an inlet tube 14 into the chamber, while the other opening covered by a gauze communicates the chamber with the ventilation system via another tube.

A gap 15 is provided at the opposite butt end of the chamber 1 at the place where the supporter and screens come out of said chamber, said gap being overlapped by a comb 16 made of capron filaments and provided with a luminescent lamp 17 located outside the chamber.

The collector described in the present invention operates as follows.

The imagos of, say, grain moth are fed via the inlet tube 14 interconnecting the insect-conveying duct with the chamber 1, into the latter wherein, upon copulation they lay eggs into the meshes of the two screens and onto the supporter 3 which are located on the convex bottom 4 of the chamber 1.

The screens and the supporter 3 are periodically set in motion by the drive shafts 6 from the motor located in the auxiliary compartment 2. In the latter the eggs laid on the screens and the supporter 3 are removed by the three rotary brushes to get into the container 13. The brushes exert upon one side of the supporter and upon both sides of the two screens.

The grain moth imagos that have died in the chamber 1 upon completing the egg-laying process are carried away on the screens through the gap 15 formed by the end wall of the chamber and the screens and, upon passing the capron-filament comb 16 that closes the gap, and the light source 17, roll down into the container 13 for dead imagos of grain moth.

The live, egg-laying imagos are retained in the chamber 1 by the capron-filament comb 16 and by the light emitted by the lamp 17 (negative phototaxis) provided oppositely to the gap 15 on the outside of the butt end of the chamber 1.

As eggs and dead imagos grow collected in the container 13 the dead imagos are removed from the drawable pans of the container. Upon getting rid of the eggs the screens and the supporter 3 come into the bath 10 with running water, provided with the guide shafts 17 and the stationary capron brushes 10, the latter cleaning the screens and the supporter 3 of dirt while these are moving.

The cleaned screens and the supporter 3 are passed over the guide shafts 7 and the tension-equalizing shafts 8 and then passed by the heater fan 12.

All the components located inside the auxiliary compartment 2, as well as its lining are made of corrosion-resistant materials.

What we claim is:

1. A collector for imagos and the eggs thereof comprising means defining a chamber and an auxiliary compartment located below said chamber; said chamber having a bottom and inlet means at one end for admitting imagos thereinto; a plurality of screens and a support for said screens adapted for the imagos to lay eggs thereon; said screens and supports being in the form of an endless conveyor adapted to move across said chamber bottom and through said auxiliary compartment by means of a drive shaft for each said screen and support located in said auxiliary compartment and at the end of said chamber opposite said one end, and a driven shaft for each said screen and support located in said auxiliary compartment and at said one end of said chamber; a plurality of rotary brushes located in said auxiliary compartment in proximity to said drive shafts for removing said eggs from said screens and support; a plurality of containers located below said brushes for catching said eggs; said drive shafts being arranged parallel to each other and at different levels with respect to said bottom and said brushes being located in between and behind said drive shafts; a washing bath located in said auxiliary compartment for cleaning said screens and support after said eggs are removed therefrom, said screens and support being arranged to pass through said bath after passing over said drive shafts and past said brushes; a plurality of brushes located in said bath to scrub said screens and support; a heater fan located in said auxiliary compartment for drying said screens and support after they emerge from said bath; tensioning means for equalizing the tension of said screens and support; and means for driving said drive shafts.

2. A collector as claimed in claim 1, wherein said chamber bottom is convex and has a radius of curvature not over 10m.

* * * * *